(12) United States Patent
Shimada et al.

(10) Patent No.: US 8,562,548 B2
(45) Date of Patent: Oct. 22, 2013

(54) REHABILITATION DEVICE AND CONTROLLING METHOD THEREOF

(75) Inventors: Kei Shimada, Saitama (JP); Ken Yasuhara, Saitama (JP); Tetsuya Ido, Saitama (JP); Shuichi Wakita, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 1031 days.

(21) Appl. No.: 12/586,227

(22) Filed: Sep. 18, 2009

(65) Prior Publication Data

US 2010/0076360 A1 Mar. 25, 2010

(30) Foreign Application Priority Data

Sep. 23, 2008 (JP) ................................. 2008-243440

(51) Int. Cl.
*A61H 3/00* (2006.01)
(52) U.S. Cl.
USPC ...................... 601/5; 601/23; 601/35; 602/23
(58) Field of Classification Search
USPC ........ 601/5, 23, 24, 33, 34, 35; 602/5, 16, 23; 600/587
See application file for complete search history.

(56) References Cited

U.S. PATENT DOCUMENTS

| | | | |
|---|---|---|---|
| 6,821,233 B1 * | 11/2004 | Colombo et al. | 601/5 |
| 2002/0026130 A1 * | 2/2002 | West | 601/23 |
| 2006/0276728 A1 * | 12/2006 | Ashihara et al. | 601/5 |
| 2009/0036815 A1 * | 2/2009 | Ido | 602/23 |
| 2009/0192414 A1 | 7/2009 | Yasuhara | |

FOREIGN PATENT DOCUMENTS

| | | |
|---|---|---|
| JP | 7-236669 | 9/1995 |
| JP | 2002-345994 (A) | 12/2002 |
| JP | 2005-006751 A | 1/2005 |
| JP | 2007-020672 A | 2/2007 |
| JP | 2007-061217 (A) | 3/2007 |

OTHER PUBLICATIONS

2005 Kyodo News © Established 1945; Medical News, "New flow to the rehabilitation of 'experience' from the 'science' to the neurophysiologist in the development of"; http://www.47news.jp/feature/medical/news/0221rehabiritation.html.

\* cited by examiner

*Primary Examiner* — Quang D Thanh
(74) *Attorney, Agent, or Firm* — Carrier Blackman & Associates, P.C.; William D. Blackman; Joseph P. Carrier

(57) ABSTRACT

The present invention provides a rehabilitation device using a walking assistance device (1) having an actuator which generates and provides torque to a lower limb joint of a wearer wearing the walking assistance device (1), comprising a floor reaction force pattern storing unit (330) configured to store a reference floor reaction force pattern; a control target floor reaction force setting unit (340) for determining a control target floor reaction force based on the floor reaction force pattern stored in the floor reaction force pattern storing unit (330); a target torque calculating unit (350) for calculating a target torque of the actuator to achieve the control target floor reaction force determined by the control target floor reaction force setting unit (340); and an actuator output controller (150) for controlling output of the actuator such that the actuator generates a torque matching the target torque calculated by the target torque calculating unit (350); wherein the floor reaction force that the wearer receives is increased and decreased by the application of torque generated by the actuator.

16 Claims, 13 Drawing Sheets

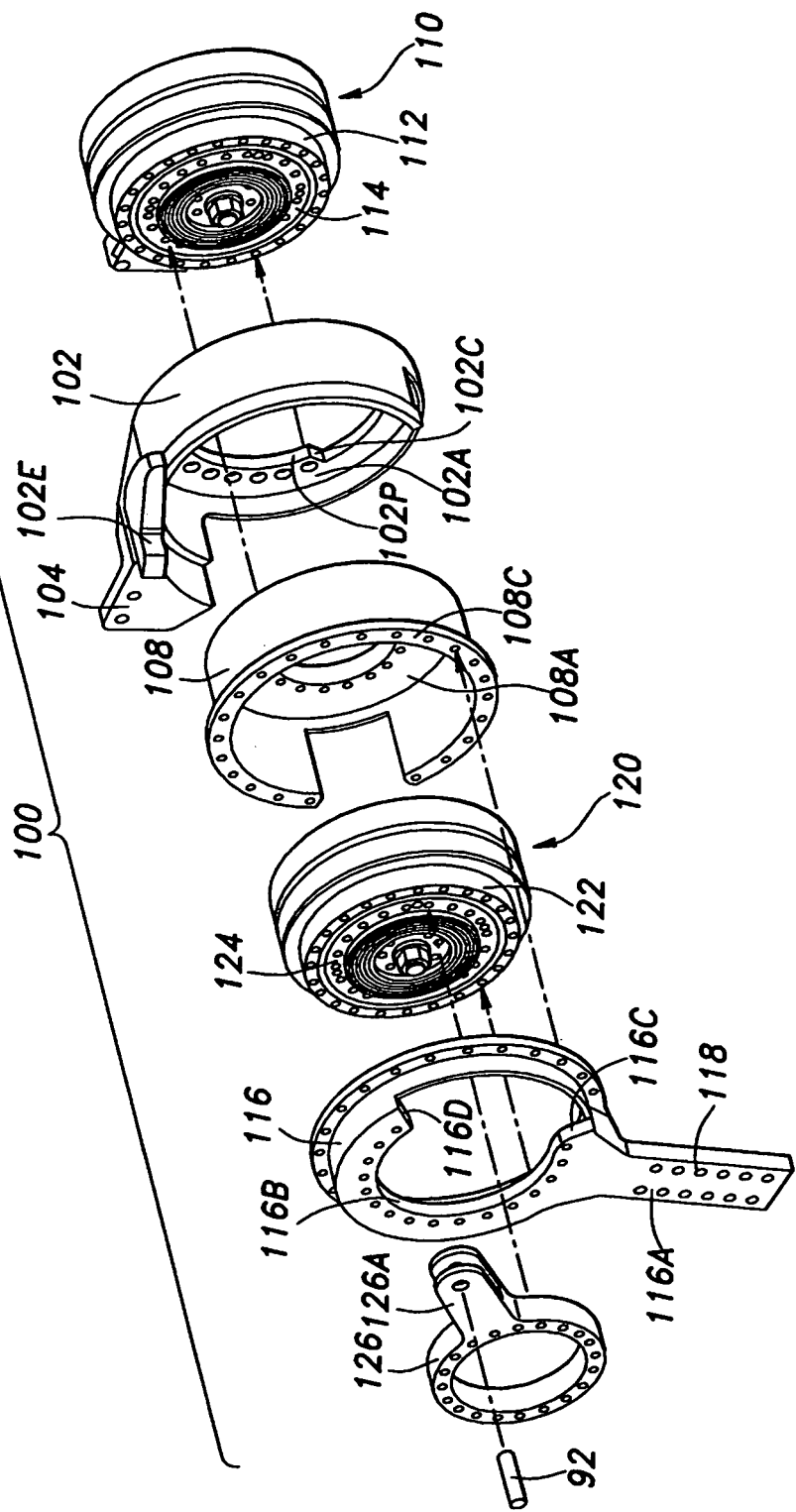

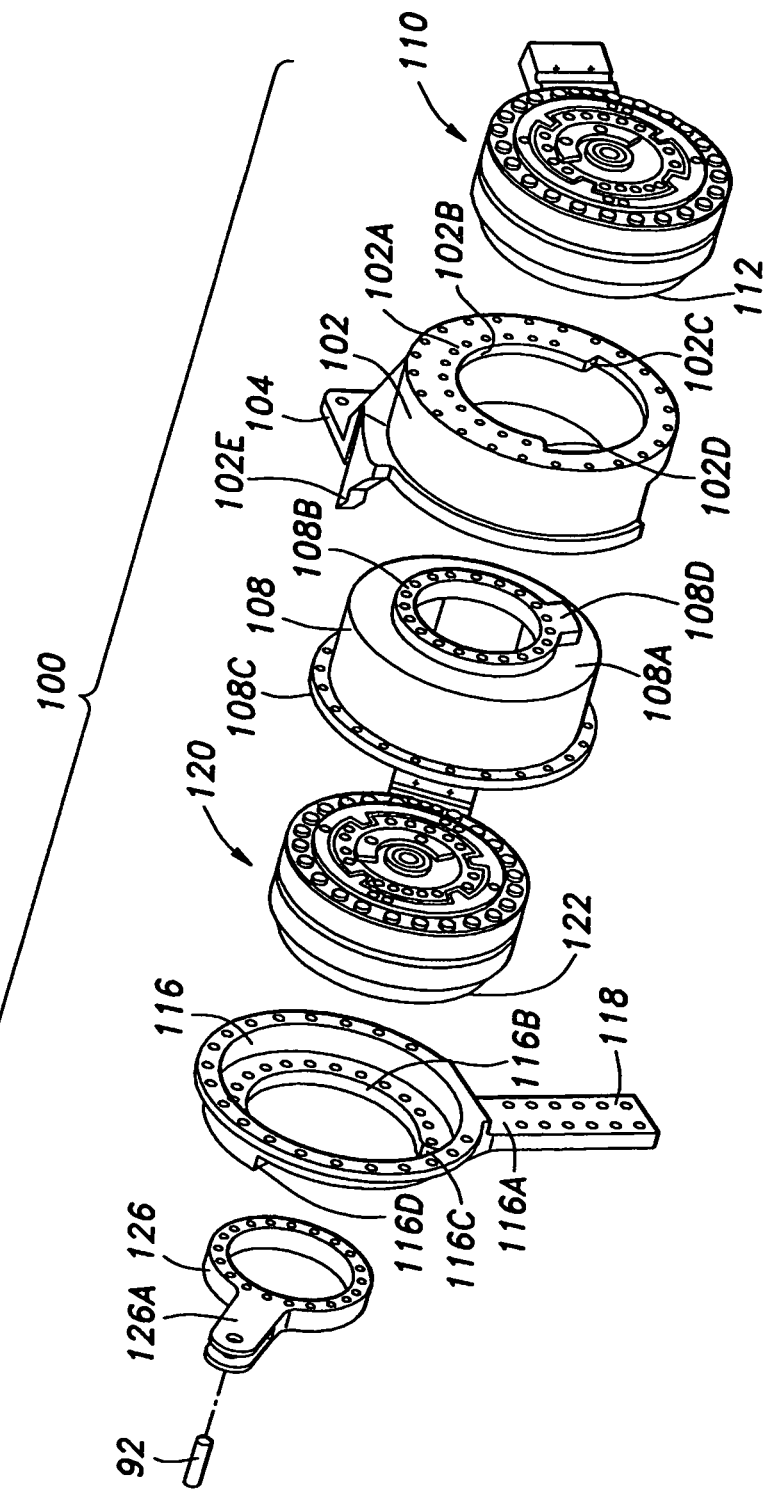

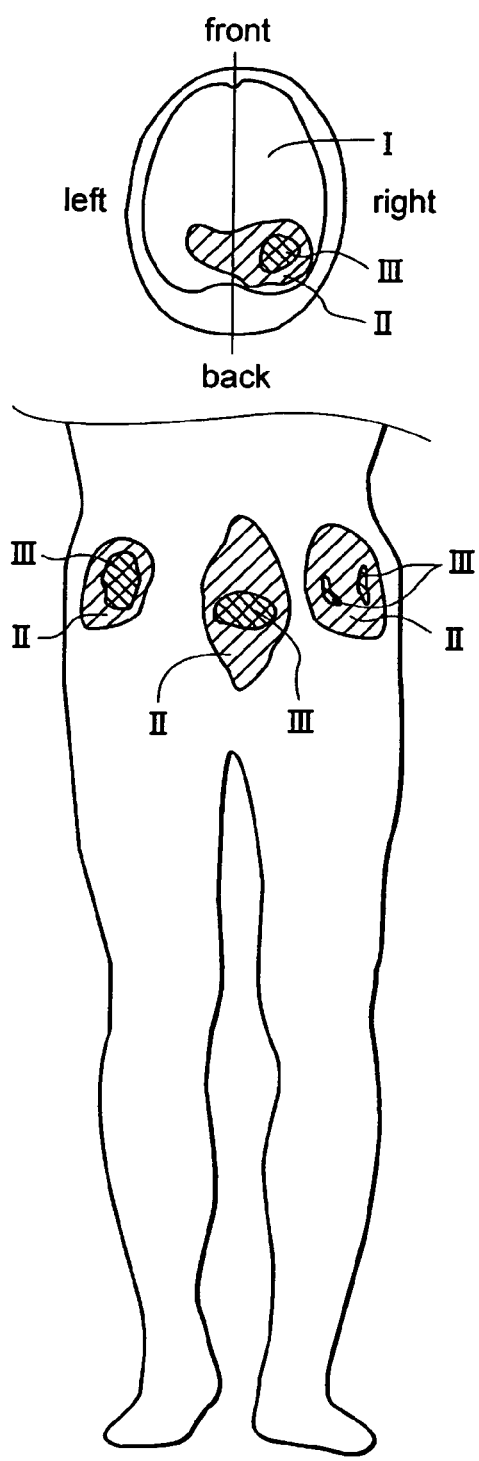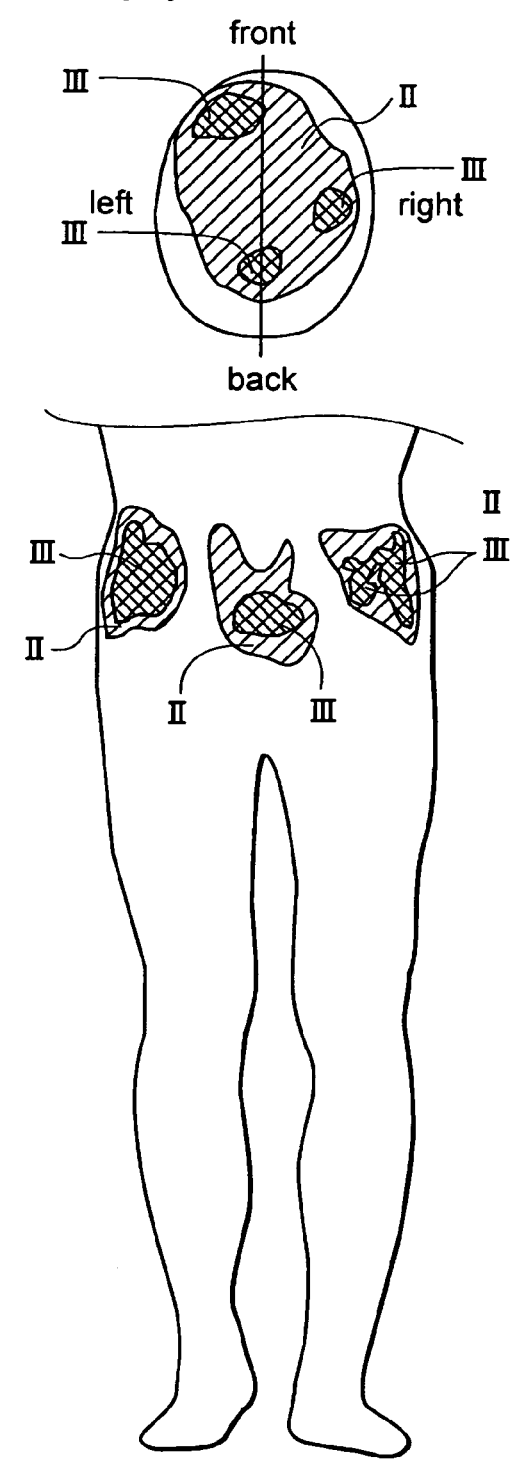
Fig. 8(A)
Fig. 8(B)

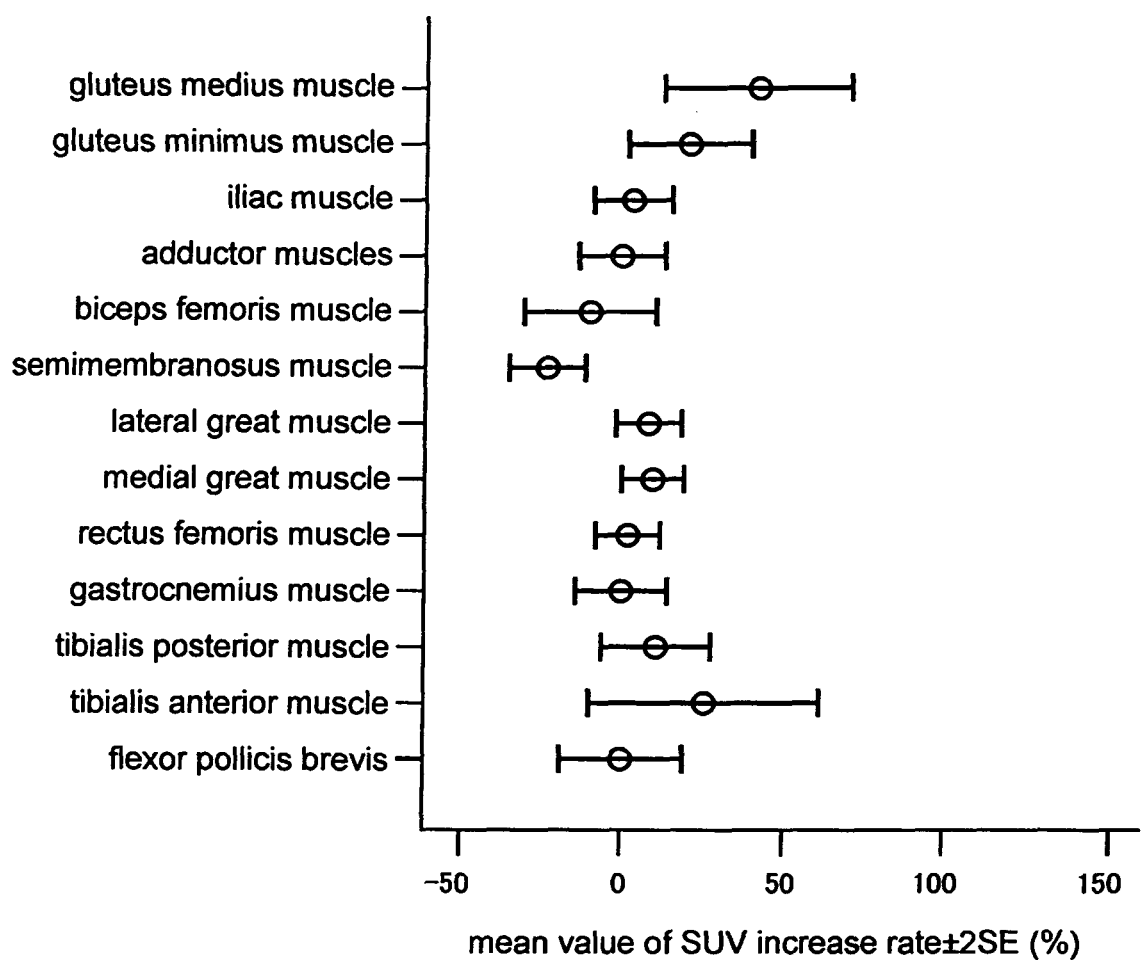

REHABILITATION DEVICE AND CONTROLLING METHOD THEREOF

TECHNICAL FIELD

The present invention relates to a rehabilitation device and a controlling method thereof, and more specifically to a rehabilitation device and a controlling method thereof for rehabilitation aiming at reconstructing cerebral tissue by providing stimulation to cerebral nervous system through walking training.

BACKGROUND OF THE INVENTION

Recently, it has been found that the recovery from motion impairment of limbs caused by cerebral infraction or cerebral stroke is closely related to the cerebral nerve activity involved in the reconstruction of brain's neural network, and a walking training consisting of walking on a power-driven caterpillar treadmill promotes the reconstruction of brain's neural network of such patient, thereby providing the effects of neurorehabilitation (for example, see http://www.47news.jp/feature/medical/ news/rehibilitation.html).

As rehabilitation devices for performing waking training, there are known devices such as the one disclosed in Japanese patent application laid open publication No. 2002-345994, which uses treadmill, and the one disclosed in Japanese patent application laid open publication No. 07-236669, which partially hoists the rehabilitant on the treadmill to reduce the load on his feet to an effective level for walking training. In addition, there is known another device which adjusts the torque generated by an actuator mounted on the hip of the user according to the motion rhythm regarding stride length and walking pace of the user and provides it to the lower limb joints (Japanese patent application laid open publication No. 2007-61217).

BRIEF SUMMARY OF THE INVENTION

In the conventional neurorehabilitation which involves walking training on a treadmill, the physicaltherapist has to provide an appropriate motion to the rehabilitant's pelvis with his hands on the rehabilitant's hip in order to facilitate the natural motion of the lower limbs, and thus this type of rehabilitation is supposed to be a burden for the physical therapist. Moreover, in this conventional neurorehabilitation, the technique of the physical therapist becomes very important for performing an effective rehabilitation, however such technique is determined by the experience, proficiency, and skill of the physical therapist, which is thought to be one of the major obstacles for the widespread use of this method.

In view of such problems of the prior art, a primary object of the present invention is to achieve a neurorehabilitation in order to reconstruct the cerebral tissue of a patient having damage in his/her brain caused by a cerebral infraction or cerebral stroke, without depending on the skill of a physical therapist.

The rehabilitation device of the present invention was conceived based on the following technical concept to resolve the above-mentioned problems.

The 1st technical concept is to effectively lead a physically impaired person, having difficulties in walking, to walk according to a reference walking pattern consisting of increasing and decreasing of floor reaction force according to the torque provided to the hip joints and knee joints (especially, to the hip joint) to assist their motion. This induces the reconstruction of the cerebral tissue, which is expected to finally enable the impaired person to walk with lower load on his/her lower limbs, and in an effective manner, without using the walking assistance device. In addition, this method improves the communication between the brain and muscles, and promotes reconstruction of a bypass route in the brain that avoids a damaged area. This method, moreover, also reduces the burden of a rehabilitation assistant, such as physical therapist.

The second one is not to provide a torque to ankles (i.e., not to assist the motion of ankles). This enables the patient to walk according to the reference walking pattern without kicking the ground and thus without having load on his/her ankles.

The third one is to lead the patient to walk with the feet tracing two mutually parallel lines, thereby enabling the patient to walk comfortably according to the reference walking pattern of a physically unimpaired person without kicking the ground too much.

The forth one is to induce the right and left lower limbs to move in a symmetrical motion pattern during walking by providing an optimum torque to each hip joint, in case that the lower limbs tend to move in an asymmetric motion pattern.

The fifth one is to enable walking rehabilitation in a prolonged period of time without the accumulation of fatigue substances by inducing the lower limb muscles to repeat a rhythmical motion cycle using torque generated by the walking assistance device.

The sixth one is to monitor cerebral activity in real-time while providing an appropriate and low load walking pattern using torque generated by the actuator of the walking assistance device. This enables to plan and conduct propriate and effective rehabilitation according to the activity of each right and left brain motor area and the degree of the reconstruction of brain tissue.

The rehabilitation device of the present invention is a rehabilitation device using a walking assistance device having an actuator which provides torque to a lower limb joint of a wearer wearing the walking assistance device, comprising a floor reaction force pattern storing unit configured to store a reference floor reaction force pattern; a control target floor reaction force setting unit for determining a control target floor reaction force based on the floor reaction force pattern stored in the floor reaction force pattern storing unit; a target torque calculating unit for calculating a target torque of the actuator to achieve the control target floor reaction force determined by the control target floor reaction force setting unit; and an actuator output controller for controlling output of the actuator such that the actuator generates a torque matching the target torque calculated by the target torque calculating unit; wherein the floor reaction force that the wearer receives is increased and decreased by the application of torque generated by the actuator.

In the rehabilitation device of the present invention, preferably, the reference floor reaction force pattern is based on floor reaction force which a physically unimpaired person receives during walking in a normal manner.

In the rehabilitation device of the present invention, preferably, the floor reaction force pattern storing unit is configured to store a plurality of floor reaction force patterns, a floor reaction force pattern is configured to be selected from the plurality of floor reaction force patterns through external manipulation, and the control target floor reaction force setting unit is configured to determine the control target floor reaction force based on the selected floor reaction force pattern.

In the rehabilitation device of the present invention, preferably, the floor reaction force pattern storing unit is configured to store a plurality of floor reaction force patterns, said rehabilitation device further comprises a cerebral activity detector for quantitatively-detecting brain activity of the wearer during walking and a floor reaction force pattern selecting unit for selecting a floor reaction force pattern from the plurality of floor reaction force patterns according to the brain activity quantitatively-detected by the cerebral activity detector, and the control target floor reaction force setting unit is configured to determine the control target floor reaction force based on the floor reaction force pattern selected by the floor reaction force pattern selecting unit.

In the rehabilitation device of the present invention, preferably, the cerebral activity detector is configured to separately-detect brain activity of a right motor area and that of a left motor area of the brain, and the floor reaction force pattern selecting unit is configured to average values of the brain activity of the right motor area and the left motor area to obtain a brain activity average value based on which the floor reaction selecting unit is configured to select the floor reaction force pattern.

In the rehabilitation device of the present invention, preferably, the cerebral activity detector is configured to separately-detect the brain activity of a right motor area and that of a left motor area of the brain, and the floor reaction force pattern selecting unit is configured to separately-select floor reaction force patterns each for a right side lower limb or left side lower limb based on the activity of the right motor area and that of the left motor area.

In the rehabilitation device of the present invention, preferably, a differential value at a given point of each of the plurality of floor reaction force patterns is different from differential values at corresponding points of other floor reaction force patterns, and an integral value at a given point of each of the plurality of floor reaction is different from integral values at corresponding points of other floor reaction force patterns.

The rehabilitation device of the present invention preferably further comprises a caterpillar-type treadmill on which the wearer walks, a hoisting unit for partially-hoisting an upper part of lower limbs of the wearer on the treadmill, and a hoisting load controller for controlling a hoisting load of the hoisting unit.

A method for controlling a rehabilitation device using a walking assistance device having an actuator which provides torque to a lower limb joint of a wearer wearing the walking assistance device, comprises determining control target floor reaction force according to a reference floor reaction force pattern which is based on floor reaction force which a physically unimpaired person receives during walking in a normal manner; calculating a target torque of the actuator for achieving the target control floor reaction force; controlling output of the actuator such that the actuator generates a torque matching the target torque calculated by the target torque calculating unit; wherein, the floor reaction force that the wearer receives is increased and decreased by the torque generated by the actuator.

According to the rehabilitation device of the present invention and the controlling method thereof, the output of the actuator mounted to the walking assistance device is controlled so as to achieve the floor reaction force pattern which is based on the floor reaction force that a physically unimpaired person receives during walking in a normal manner, and is provided to the lower limb joint of the wearer.

Accordingly, the walking assistance device of the rehabilitation device of the present invention plays a role equivalent to that of a physical therapist who applies facilitation technique, and thus enables effective walking training based on the reference walking pattern of a physically unimpaired person by providing torque to lower limb joints. Therefore, the rehabilitation device of the present invention is expected to achieve neurorehabilitation that promotes the reconstruction of cerebral tissue of a patient having damage in brain tissue caused by cerebral infraction or cerebral stroke without depending on the facilitation technique of the physical therapist.

BRIEF DESCRIPTION OF THE DRAWINGS

FIG. 3 is a right side exploded perspective view showing the power generator used for the walking assistance device of the embodiment 1.

FIG. 4 is a left side exploded view showing the power generator used for the walking assistance device in the embodiment 1.

FIG. 8 shows the PET image and hemoglobin concentration image taken after conducting walking exercise without the walking assistance device (A) and the same images taken after conducting walking exercise using the walking assistance device (B).

FIG. 9 is a graph showing the SUV increase rate of each muscle.

DETAILED DESCRIPTION OF THE PREFERRED EMBODIMENTS

An embodiment of the rehabilitation device according to the present invention is described below with reference to FIGS. 1-4.

Figure 1:
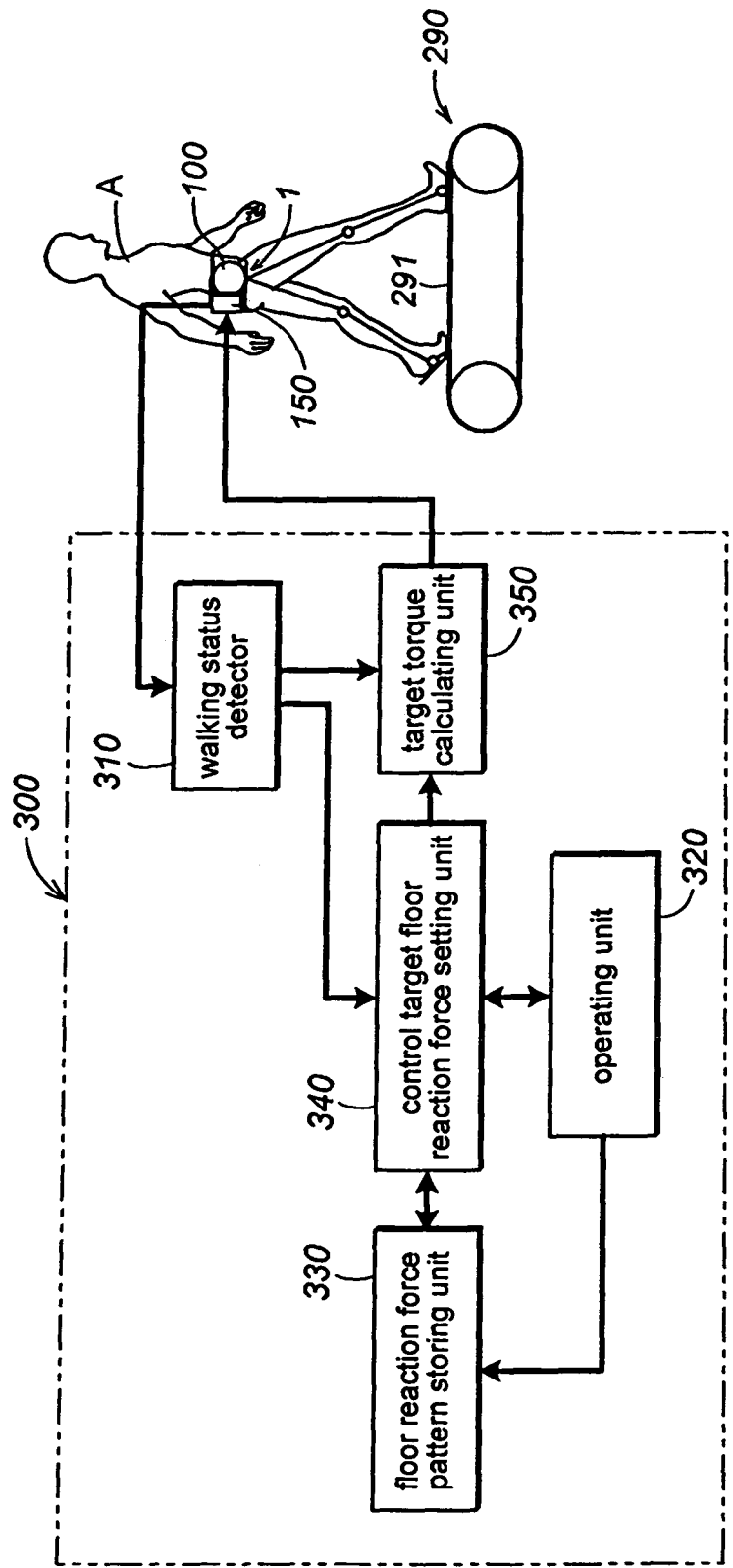
FIG. 1 is a schematic illustration showing an embodiment (embodiment 1) of the rehabilitation device according to the present invention.

As shown in FIG. 1, the rehabilitation device according to the present embodiment uses a walking assistance device 1 worn on limbs of a person (patient A) and having actuators which generates and provides torque to lower limb joints of the patient A. The patient A wearing the walking assistance device performs walking training on a treadmill 290 using the torque generated by the actuators of the walking assistance device 1.

The treadmill 290 is an electric running machine having a caterpillar belt 291 driven by an electric motor, and thus enables walking on a fixed point. In this case, the walking rate of the patient A on the caterpillar belt 291 is determined by the driving speed of the caterpillar belt 291. Therefore, the walking rate of the patient A can be controlled by controlling the driving speed of the caterpillar belt 291.

The actuators of the walking assistance device 1 generate torque and provides it to lower limb joints, and increases and decreases the floor reaction force that the patient A receives. Next is explained an example of a preferable walking assistance device 1 for the present embodiment of the rehabilitation device with reference to FIG. 2.

Figure 2:
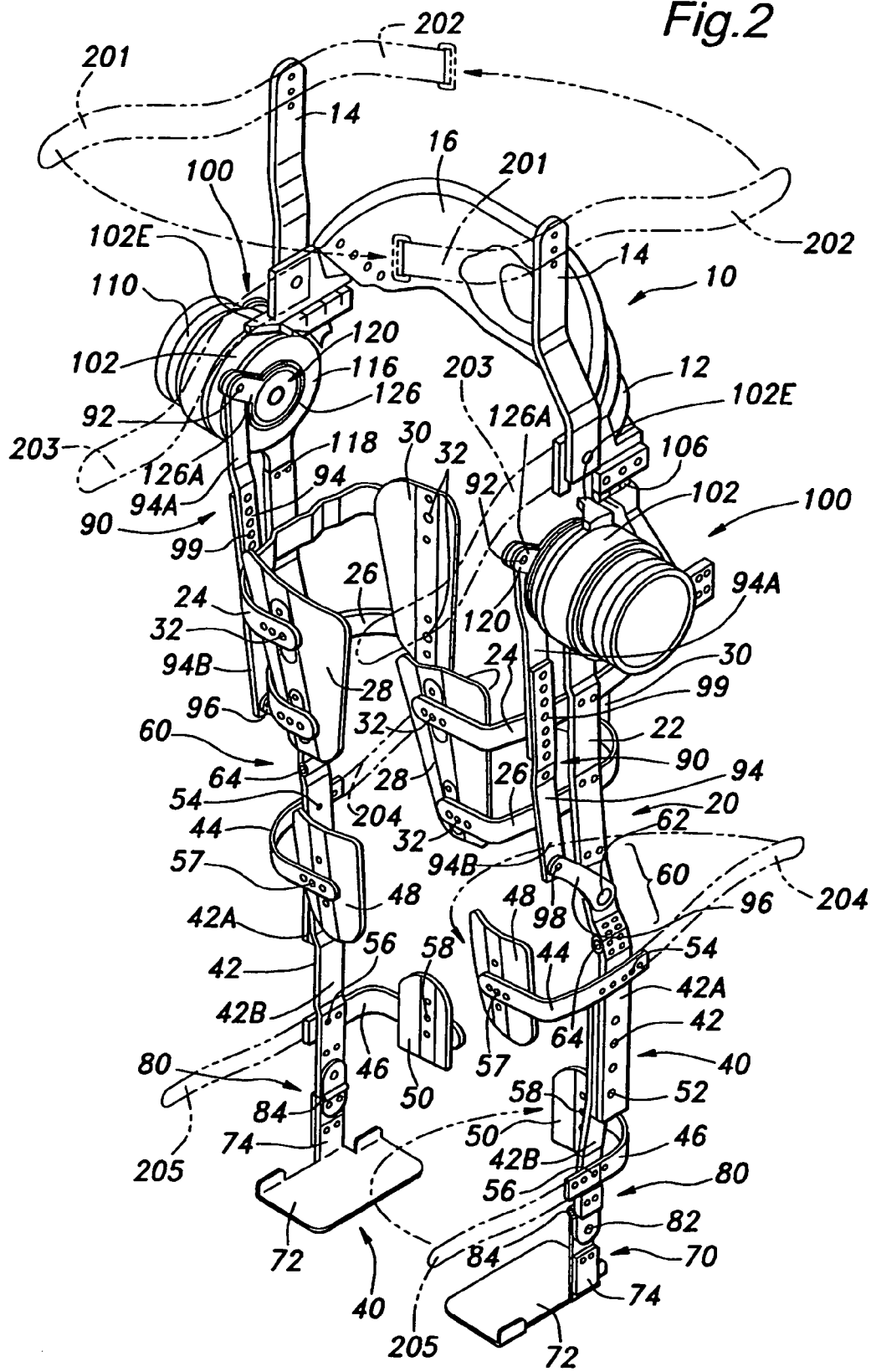
FIG. 2 is a perspective view showing an embodiment the walking assistance device used in the rehabilitation device according to the present invention.

As shown in FIG. 2, the walking assistance device 1 mainly comprises a pelvis support member 10 adapted to be worn on the pelvis of a wearer, right and left thigh support members 20 adapted to be worn on the right and left thighs of the wearer, right and left leg support members 40 adapted to be worn on the right and left legs of the wearer, right and left knee joint hinges 60 disposed at positions corresponding to side parts of the right and left knee joints of the wearer and connecting the leg support members 40 to the thigh support members 20 in a manner that enables back-and-forth rotation of the leg support members 40 with respect to the thigh support members 20, right and left foot support members 70 adapted to support the feet of the wearer, and right and left foot joint hinges 80 disposed at positions corresponding to side parts of the right and left foot joints of the wearer and connecting the foot support members 70 to the leg support members 40 in a manner that enables back-and-forth rotation of the foot support members 70 with respect to the leg support members 40.

The walking assistance device 1 further comprises right and left power generator assemblies (actuators) 100 mounted to the pelvis support member 10 at positions corresponding to side parts of the right and left hip joints of the wearer, and right and left power transmitting mechanisms 90.

The pelvis support member 10 comprises a metal pelvis frame 12 having the shape of letter-C as seen in plan view so as to engage the dorsal part of the pelvis, a pair of lateral support frames 14 each attached to either end of the frontal part of the pelvis frame 12, and a back pad 16 attached to the pelvis frame 12. The back pad 16 has a portion which abuts the sacral bone of the wearer when the device is worn. This portion contains a sponge and the like and thus is provided with elasticity. The lateral support frames 14 are provided with adjustable body trunk belts 201, 202 for securing the lateral support frames 14 to the body trunk. The pelvis frame 12 is provided with, at either end, an adjustable abdominal belt 203 so that the pelvis frame 12 fits the pelvis. The abdominal belt 203 may be adjusted by hook and loop fastener.

Each of the thigh support members 20 comprises a vertical bar 22, letter-C shaped springy pad support members 24 and 26 mounted, one above the other, to the vertical bar 22, a frontal thigh pad 28 attached to the frontal part of the pad support members 24 and 26 so as to abut the frontal part of the thigh of the wearer, and a dorsal thigh pad 30 attached to the dorsal part of the pad support members 24 and 26 so as to abut the dorsal part of the thigh of the wearer.

In detail, each of the pad support members 24 and 26 is fixed at its middle point to the internal surface of the vertical bar 22 in a horizontal posture, and thus extends forward and backward from the vertical bar 22. The frontal thigh pad 28 is fixed to the frontal part of the pad support members 24 and 26 such that it bridges the pad supports members 24 and 26. The dorsal thigh pad 30 is fixed to the dorsal part of the pad support members 24 and 26 such that it bridges the pad supports members 24 and 26. Thus the dorsal thigh pad 30 and the frontal thigh pad 28 are arranged at the same height in opposed positions.

Each of the frontal thigh pad 28 and the dorsal thigh pad 30 is secured by bolts at a middle point in the width direction to the pad support members 24 and 26 at an attaching portion 32. The attaching portion 32 includes a plurality of bolt holes so that the position of each pad can be adjusted both vertically and horizontally.

The frontal thigh pad 28 and dorsal thigh pad 30 may be made of metal or plastic and have elasticity to fit the thigh of the wearer.

Each of the leg support members 40 comprises a vertical bar 42, a letter-L shaped springy pad support member 44 attached to the upper end of the vertical bar 42 and extending forward therefrom, a letter-L shaped springy pad support member 46 attached to the lower end of the vertical bar 42 and extending backward therefrom, a frontal leg pad 48 attached to an end of the pad support member 44 so as to abut the frontal part of the leg of the wearer near the knee, a leg belt 204 attached to the pad support member 44 for fitting the frontal leg pad 48, a dorsal leg pad 50 attached to an end of the pad support member 46 so as to abut the dorsal part of the leg of the wearer near the malleolus, and a leg belt 205 attached to the pad support member 46 for fitting the dorsal leg pad 50. The dorsal leg pad 50 and the frontal leg pad 48 are arranged at different heights in opposed positions.

In detail, the vertical bar 42 consists of an upper member 42A and a lower member 42B which are secured to each other by bolts at an attaching portion 52. The attaching portion 52 includes a plurality of bolt holes so that the vertical bar 42 can be adjusted lengthwise. The pad support member 44 is secured by bolts to the upper member 42A at an attaching portion 54. The attaching portion 54 includes a plurality of bolt holes so that the position of the pad support member 44 can be adjusted horizontally. The pad support member 46 is secured by bolts to the lower member 42B at an attaching portion 56. The attaching portion 56 includes a plurality of bolt holes so that the position of the pad support member 56 can be adjusted horizontally.

The frontal leg pad 48 is secured to the frontal end of the pad support member 44 by bolts at an attaching portion 57. The attaching portion 57 includes a plurality of bolt holes such that the position of the frontal leg pad 48 can be adjusted vertically and horizontally. The dorsal leg pad 50 is secured to the back-end of the pad support member 46 by bolts at an attaching portion 58. The attaching portion 58 includes a plurality of bolt holes such that the position of the dorsal leg pad 50 can be adjusted vertically and horizontally.

Therefore, the positions of the frontal leg pad 48 and dorsal leg pad 50 can be adjusted according to the body type and size of the wearer. The leg belts 204 and 205 may be adjusted by hook and loop fastener.

The frontal thigh pad 28, the dorsal thigh pad 30, the frontal leg pad 48 and the dorsal leg pad 50 may each be made of metal plate or plastic and have elasticity to fit on the thigh and the leg of the wearer.

The knee joint hinge 60 is disposed at a position corresponding to a side part of the knee joint of the wearer, and connects the upper end of the vertical bar 42 of the leg support member 40 to the lower end of the vertical bar 22 of the thigh support member 20 via a shaft 62 in a manner that enables back-and-forth rotation of the vertical bar 42 with respect to the vertical bar 22. The knee joint hinge 60 has a hinge element 64 so that it can rotate in a lateral direction of the wearer around the hinge element 64 in addition to back-and-forth rotation.

The foot support member 70 comprises a sole supporting plate 72 which supports the sole of the wearer and receives floor reaction force, and a vertical bar 74 extending vertically upward from the sole supporting plate 72. The vertical bar 74 may be length-adjustable.

The foot joint hinge 80 is disposed at a position corresponding to a side part of the foot joint of the wearer and connects the upper end of the vertical bar 74 of the foot support member 70 to the lower end of the vertical bar 42 of the leg support member 40 via a pivot 82 so as to enable back-and-forth rotation of the vertical bar 74 with respect to the vertical bar 42. The foot joint hinge 80 has a hinge element 84 so that it can rotate in a lateral direction of the wearer around the hinge 84 in addition to back-and-forth rotation around the pivot 82.

Next, a power generator assembly 100 is explained in detail with reference to FIGS. 2 and 3. The power generator 100 comprises a hip joint electric motor 110, which is a power generator for the hip joint, and a knee joint electric motor 120, which is a power generator for the knee joint, on the same axis. The hip joint electric motor 110 and knee joint electric motor 120 each have a rotary encoder for detecting the rotation angle of the hip joint electric motor 110 and that of the knee joint electric motor 120, respectively.

The power generator 100 comprises a cylindrical fixed case member 102 and an intermediate coupling cylinder 108 rotatably engaged inside the fixed case member 102. The fixed case member 102 is provided with an attaching piece 104 extending outward at which it is attached to a hinge 106 mounted to the lower end of the pelvis frame 12 of the pelvis support member 10 so that it can rotate in a lateral-direction of the wearer.

The hip joint electric motor 110 is a rotary motor comprising a stator member 112 and a rotor member 114 mounted inside the stator member 112 such that it can rotate with respect to the stator member 112 around their axis. The stator member 112 is secured by bolts to the external surface of an end 102A of the fixed case member 102.

The intermediate coupling cylinder 108 has, on its end 108A, a ring extension 108B which rotatably engages with an central opening 102B provided to the end 102A of the fixed case member 102. The rotor member 114 of the hip joint electric motor 110 is secured by bolts to the ring extension 108B of the intermediate coupling cylinder 108. Thus, the intermediate coupling cylinder 108 and the rotor member 114 of the hip joint electric motor 110 rotate in an integrated manner.

The intermediate coupling cylinder 108 is provided with a flange 108C at the other end (i.e., the end opposite to the end 108A). The flange 108C is secured by bolts to an output member 116. The output member 116 has, in an integrated manner, an arm 116A extending radially outward. The arm 116A is secured by bolts to the vertical bar 22 of the thigh support member 20 at an attaching portion 118. The attaching portion 118 includes a plurality of bolt holes so that the arm 116A can be secured to the vertical bar 22 in a length-adjustable manner.

The knee joint electric motor 120 is a rotary motor comprising a stator member 122 engaged inside the intermediate coupling cylinder 108, and a rotor member 124 mounted inside the stator member 122 such that it can rotate with respect to the stator member 122 around the axis. The stator member 122 is secured by bolts to the output member 116. Therefore, the stator member 122 of the knee joint electric motor 120 is integrally connected to the rotor member 114 of the hip joint electric motor 110.

The rotor member 124 of the knee joint electric motor 120 is secured by bolts to an output member 126. The output member 126 is rotatably-fitted into a central opening 116B formed in the output member 116 of the hip joint electric motor 110 and protrudes outward from the central opening 116B.

The output member 126 has, in an integrated manner, an arm 126A extending radially outward. As shown in FIG. 1, the arm 126A is pivotally connected to the upper end of a link 94 of the power transmitting mechanism 90 by a pivot pin 92.

The shaft 62 of the knee joint hinge 60 is fixed to the upper end of the vertical bar 42 of the leg support member 40 and to an end of an arm 96 which is a component of the power transmitting mechanism 90. Thus the arm 96 is fixedly attached to the vertical bar 42 of the leg support member 40. The arm 96 is pivotally connected, at the other end, to the lower end of the link 94 by a pivot pin 98.

The distance between the rotation center of the rotor member 124 of the hip joint electric motor 120 and one of link 94's pivot points which is formed by the pivot pin 92 is equal to that between the center of the shaft 62 and the other link 94's pivot point which is formed by the pivot pin 98. Therefore, the power transmitting mechanism 90 forms a parallelogram linkage structure along with the vertical bar 22 for transmitting the rotation of the rotor member 124 of the knee joint electric motor 120 to the vertical bar 42 of the leg support member 40.

The link 94 comprises an upper member 94A and lower member 94B. Both members are secured to each other by bolts at an attaching portion 99 which includes a plurality of bolt holes so that these members can be secured to each other in a length-adjustable manner.

As shown in FIGS. 3 and 4, the ring extension 108B of the intermediate coupling cylinder 108 is provided with a movable stopper 108D. The central opening 102B of the fixed case member 102 is provided with stopper walls 102C and 102D, separated from each other at a predetermined rotation angle, for holding the movable stopper 108D. Thus, the maximum rotation angle range of the rotor member 112 of the hip joint electric motor 110 with respect to the fixed case member 102 is determined by the angle between the stopper walls 102C and 102D which form the first stopper mechanism together with the movable stopper 108.

As a result, the motion of the hip joint is limited to, for example, 90 degrees of flexion, and 30 degrees of extension, thereby achieving the motion of the hip joint in normal and natural walking.

The arm 126A of the output member 126 of the knee joint electric motor 120 serves as a movable stopper. The central opening 116B of the output member 116 of the hip joint electric motor 110 is provided with stopper walls 116C and 116D, each separated from each other at a predetermined rotation angle, for holding the arm 126A. Thus, the maximum rotation angle range of the rotor member 124 of the knee joint electric motor 120 with respect to the rotor member 114 of the hip joint electric motor 110 is determined by the angle between the stopper walls 116C and 116D which form the second stopper mechanism together with the arm 126A.

As a result, the motion of the knee joint is limited to, for example, 90 degrees of flexion, and 0 degree of extension, thereby achieving the motion of the knee joint in normal and natural walking.

As a third stopper mechanism for determining the maximum rotation angle range of the rotor member 124 of the knee joint electric motor 120 with respect to the fixed case member 102, a stopper 102E is integrally-mounted to the fixed case member 102 for limiting the rotation of the arm 126A of the output member 126 in a door-stop manner.

In this embodiment, although the rotation range of the hip joint and that of the knee joint are set to be 90 degrees of flexion—30 degrees of extension and 0 degree of extension—90 degrees of flexion, respectively, which are safe in terms of each joint motion, if the wearer flexes the hip joint 90 degrees and extends the knee joint (0 degree of extension) the wearer may over-lengthen and damage his/her knee tendon. This is caused by the biarticular muscle structure of the hamstrings located in the back part of the thigh and linking the pelvis to the leg.

The third stopper mechanism is provided to prevent such a lesion of the hamstrings by preventing the extension of the knee joint from 45 degrees of flexion when the hip joint is flexed 90 degrees. Thus, by mounting a mechanical stopper for the output member 126 of the knee joint electric motor 120 to the stator portion of the hip joint electric motor 110, the extension angle of the knee joint becomes dependent to and limited by the rotation angle of the hip joint.

When using the walking assistance device 1 of the above configuration, the wearer places his/her feet on the sole supporting plates 72 of the foot support members 70, wears the pelvis support member 10 on the pelvis, fastens the abdominal belt 14, and puts on the thigh support member 20 with the frontal thigh pad 28 and dorsal thigh pad 30 abutting the frontal and dorsal part of thigh, respectively.

The pelvis support member 10 is provided with a power supply unit and control unit (not shown). The control unit comprises a driving circuit and electronically-controlled actuator output controller 150 for the hip joint electric motor 110 and the knee joint electric motor (FIG. 1).

The actuator output controller 150 controls the output of the hip joint electric motor 110 and that of the knee joint electric motor 120 such that each motor generates torque matching corresponding control target torque calculated by a target torque calculating unit 350 which is described below. This output torque control is performed separately for each of the right and left hip joint electric motors 110 and right and left knee joint electric motors 120.

Under the above-mentioned output torque control, the hip joint electric motor 110 is driven, and the rotation of the rotor 114 is transmitted to the thigh support member 20 via the intermediate coupling cylinder 108 and the output member 116. As a result, the output torque of the hip joint electric motor 110 is provided to the hip joint of the patient A.

Also, under the above-mentioned output torque control, the knee joint electric motor 120 is driven, and the rotation of the rotor 124 is transmitted to the leg support member 40 via the output member 126 and the transmitting mechanism 90. As a result, the output torque of the knee joint electric motor 120 is provided the knee joint of the patient A.

The rehabilitation device according to the present embodiment has a control console 300, as shown in FIG. 1. The control console 300 is electronically operated and has a walking status detector 310, operating unit 320, floor reaction force pattern storing unit 330, control target floor reaction force setting unit 340, target torque calculating unit 350.

The walking status detector 310 receives output signals from the rotary encoders (not shown) of the hip joint electric motors 110 and knee joint electric motors 120, as well as current values of the hip joint electric motors 110 and knee joint electric motors 120.

The walking status detector 310 calculate the flexion angle of each of the right and left hip joints (joint angle θa) based on the signals from the rotary encoders of the right and left hip joint electric motors 110 as well as the flexion angle of each of the right and left knee joints (joint angle θb) based on the signals from the rotary encoders of the right and left knee joint electric motors 120. The joint angles θa and θb, which have been calculated by the walking status detector 310 are then inputted into the control target floor reaction force setting unit 340.

The walking status detector 310 calculates the actual output torque of each of the hip joint motors 110 and knee joint motors 120 based on their current values, and then sends signals indicating these actual output torques to the target torque calculating unit 350.

In addition, the walking status detector 310 may receive signals from 6-axis force sensors (not shown) mounted on connection sites between pad support members 24, 26 and vertical bar 22 and/or on connection sites between pad support members 44, 46 and vertical bar 42, if needed. The walking status signal detector may also receive signals from floor reaction force sensors (not shown) mounted to the foot support plates 72 to calculate the actual floor reaction force of each lower limb and may send it as signal to the target torque calculating unit 350, if needed.

The control target floor reaction force setting unit 340 receives a floor reaction force pattern from the floor reaction force pattern storing unit 330, and then determines target control floor reaction force F* as a dependent variable against joint angles θa, θb as independent variables, based on the floor reaction force pattern, and then sends it to the target torque calculating unit 350. The floor reaction force control target value F* is determined according to the combination of the torque of the hip joint electric motor and that of the knee joint electric motor.

The target torque calculating unit 350 calculates and determines target torque for each of the hip joint electric motors and knee joint electric motors so as to achieve the floor reaction force control target value F* corresponding to each motor.

The target torque calculating unit 350 calculates a control deviation on the basis of the actual output torque, actual floor reaction force, which were received from the walking status detector 310, and floor reaction force control target value F*, and then sends a target torque command value to the actuator output control unit 150 in a feedback compensatory manner.

The floor reaction force pattern stored in the floor reaction force storing unit 330 is a pattern where the control target floor reaction force changes as a dependent value according to the lower limb joint angles (θa and θb) as independent values.

Figure 5A:
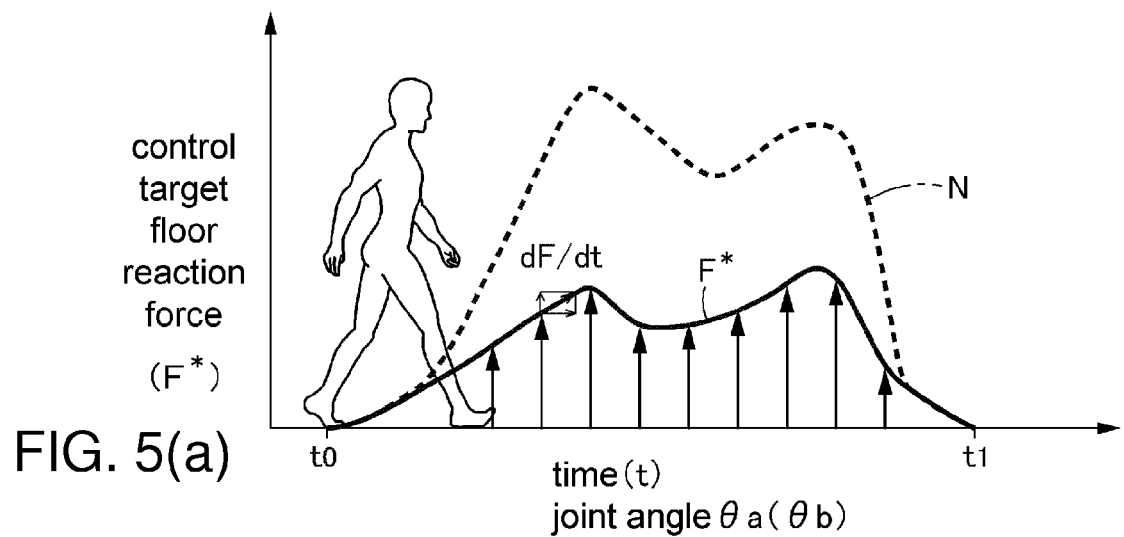
FIG. 5 (a)-(c) each is a graph showing an example of the walking assistance pattern of the walking assistance device of the rehabilitation device according to the embodiment 1.
Figure 5B:
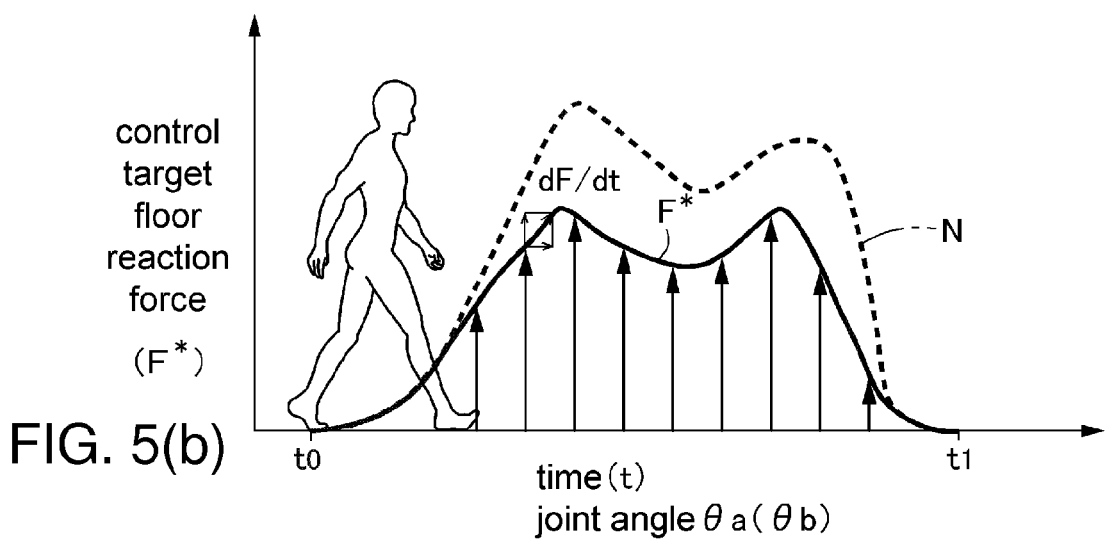
Figure 5C:
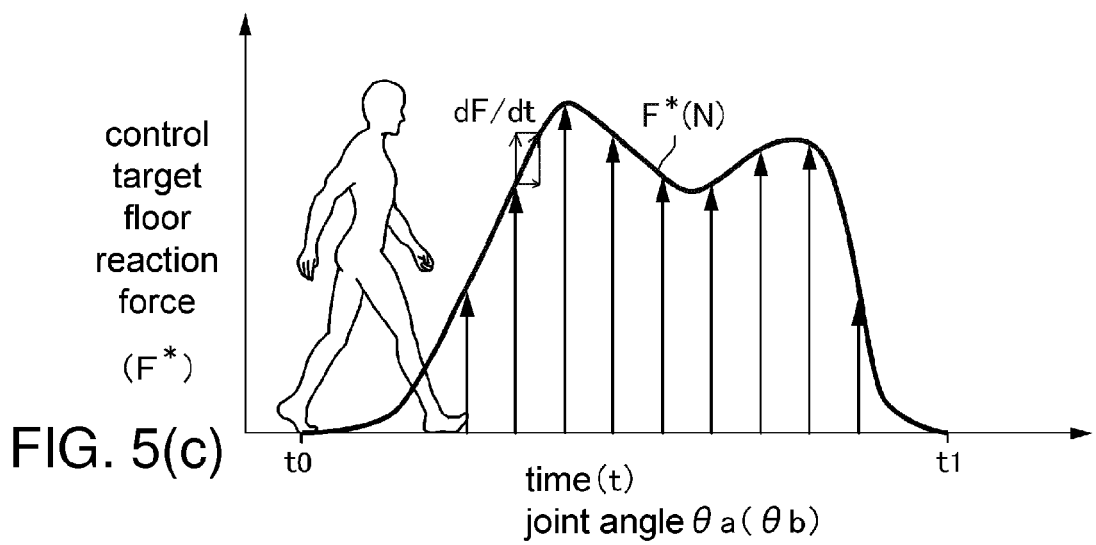

In this embodiment, as shown in FIG. 5 (a)-(c), the floor reaction force pattern storing unit 330 stores a variety of floor reaction force patterns. A differential value dF/dt of the floor reaction force at a given point of each pattern is different from differential values at corresponding points of other patterns, and an integral value $\sim(t1-t0)Fdt$ of the floor reaction force of each pattern is different from the corresponding integral values of other patterns. If the speed of the caterpillar 291 of the treadmill 290 is set to a predetermined value, the time t can be substituted for the joint angles θa and θb.

The floor reaction force patterns shown in FIG. 5 (a)-(c) each determine the control target floor reaction force F* for joint angles θa and θb on the basis of a floor reaction force pattern N of reference walking. In this embodiment, the reference walking refers to the normal walking of a physically unimpaired person and may also be determined based on the facilitation technique of the physical therapists.

The floor reaction force patterns shown in FIG. 5 (a)-(c) each have a generally similar curve to that of the floor reaction force pattern N of the reference walking. The floor reaction force pattern of FIG. 5 (a) has a smaller differential value dF/dt and integral value $\int(t1-t0)Fdt$ of the floor reaction force compared to those of the floor reaction force pattern N of the reference walking, and thus is suited for the initial stage of rehabilitation. The floor reaction force pattern of FIG. 5 (b) has a differential value dF/dt and integral value $\int(t1-t0)Fdt$ of the floor reaction force that are smaller than those of the floor reaction force pattern N of the reference walking but are bigger than those of the pattern of FIG. 5 (a), which is used in the initial stage of rehabilitation, and thus is suited for the middle stage of rehabilitation. The floor reaction force pattern of Figure (c) has the same differential value dF/dt and integral value $\int(t1-t0)Fdt$ of the floor reaction force as those of the floor reaction force pattern N of the reference walking, and thus is suited for the late stage of rehabilitation.

The operating unit 300 is a man-machine interface comprising an input device such as key board and a monitor, and is operated by an operator such as a physical therapist. The operator selects a floor reaction force pattern to be used from the floor reaction force patterns stored in the floor reaction force pattern storing unit 330 through operating unit 300.

Therefore, the operator can select a floor reaction force pattern from the patterns shown in FIG. 5 (a)-(c), which are for initial, middle, and late stage of rehabilitation, respectively, according to rehabilitation progress.

Figure 6:
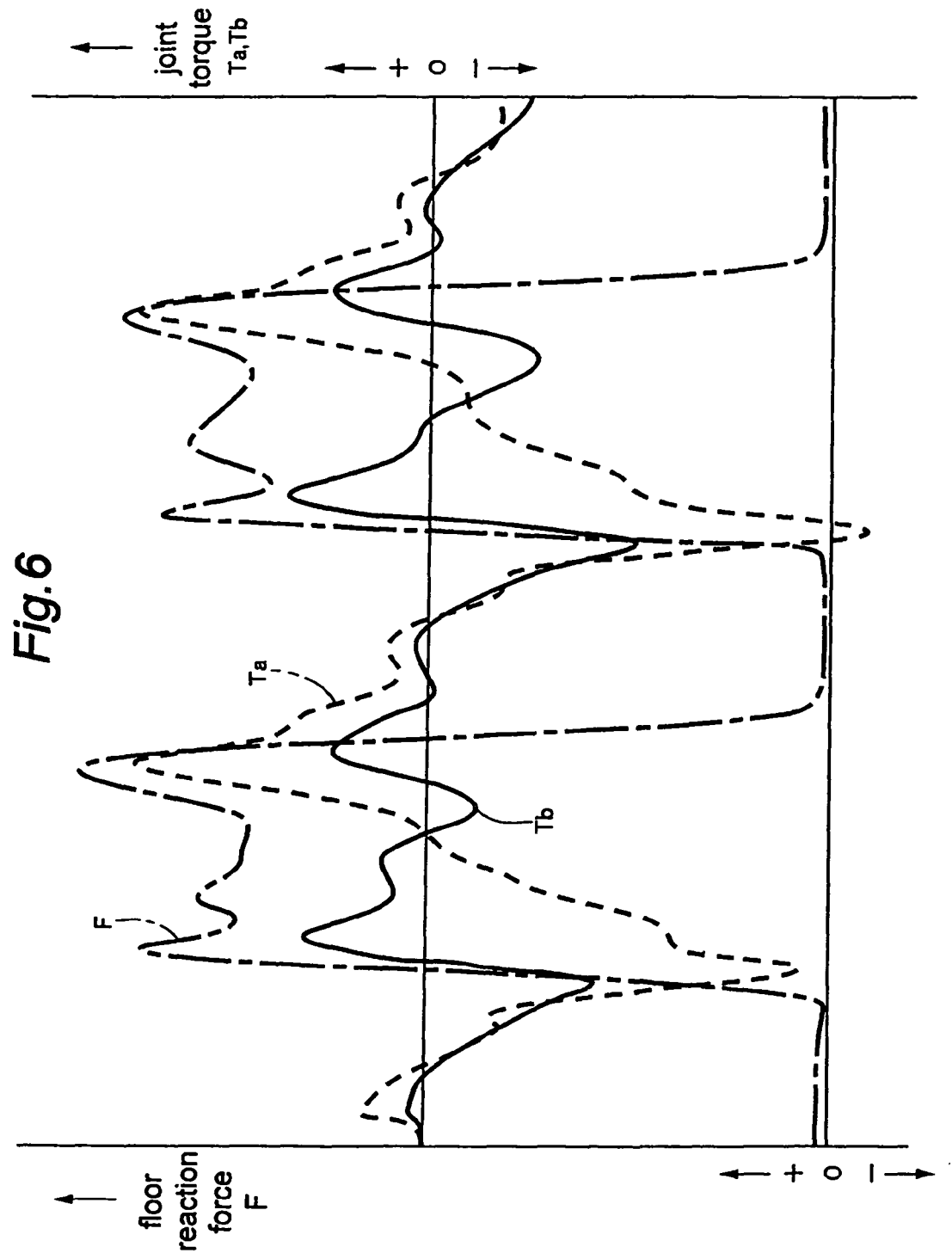
FIG. 6 is a graph showing the relation between the floor reaction force and joint torque.

FIG. 6 shows the correlation between the floor reaction force and the hip/knee joint torque in the reference walking. In FIG. 6, F represents floor reaction force, Ta represents hip joint torque, and Tb represents knee joint torque. As shown in FIG. 6, there is a correlation between the floor reaction force F and the hip joint torque Ta/knee joint torque Tb: the floor reaction force tends to increase when the hip joint torque Ta and knee joint torque Tb increase. Therefore, the target torque calculating unit 350 can convert the floor reaction force into joint torque based on the correlation property of floor reaction force joint torque shown in FIG. 6.

To undergo rehabilitation using the rehabilitation device of this embodiment, the patient A wears the walking assistance device 1, and a floor reaction force pattern is selected according to his/her rehabilitation progress. Next, the patient A gets on the caterpillar belt 291 of the treadmill 290, and then the caterpillar 291 is driven at a constant speed and the walking assistance device is activated.

Accordingly, torque determined and generated according to the selected floor reaction force pattern is provided to each of the right and left hip joints and knee joints. Therefore, the patient A can receive on his/her lower limbs the same floor reaction force pattern that a physically unimpaired person would receive during walking in a normal manner by providing appropriate torque to each lower limb joint. This leads the patient A to achieve normal walking motion of a physically unimpaired person, thereby enhancing his/her recovery from walking impairment.

As the floor reaction force is correlated with nervous stimulation, the nervous system of the patient A can be stimulated significantly by providing him/her with the floor reaction force that a physically unimpaired person receives during normal walking. Therefore, by performing effective walking rehabilitation using the walking assistance device 1, the effects of neurorehabilitation can be obtained, and thus the cerbral tissue of a patient having damage therein due to cerebral infraction or cerebral stroke can be reconstructed effectively.

As mentioned above, in this rehabilitation, the torque generated by the actuators of the walking assistance device 1 is provided to the hip joints and knee joints. Especially, by providing torque to the hip joints, and thus assisting the motion of the hip joints intensively, a reference walking pattern can be provided to the lower limbs effectively. This achieves brain reconstruction, thereby leading the patient to be able to perform effective walking on his/her own without the walking assistance device finally. In addition, the communication between the brain and muscles can be improved and a new communication bypass route avoiding the damaged area in the brain may be formed.

In such rehabilitation using the walking assistance device 1, walking assistance equivalent to the facilitation technique of a physical therapist is achieved by applying torque generated by the actuators of the walking assistance device 1. Therefore, this rehabilitation method enables effective neurorehabilitation without depending on the experience, skill, technique of the physical therapist in charge, thereby reducing the burden of the physical therapist in charge at the same time.

The walking assistance device 1 assists the hip and knee joints, but not the ankles, and thus it can provide, without causing loads on the ankles, a reference walking pattern which enables the patient to move forward easily with the feet tracing two mutually parallel lines without kicking the ground.

Moreover, during the walking assistance performed by the walking assistance device 1, a rhythmical muscular cycle is repeated without the accumulation of fatigue substances, thereby enabling walking rehabilitation for a prolonged period of time.

In order not to cause loads on patient's brain, the floor reaction force pattern is changed according to rehabilitation progress such that the magnitude, the maximum peak, and change rate of the floor reaction force increase with rehabilitation progress.

In case of dividing the rehabilitation period in 3 stages consisting of initial, middle, and late stage, in the initial stage of rehabilitation, a floor reaction force pattern where the magnitude, the maximum peak, and change rate of the floor reaction force are small may be selected so as to provide the floor reaction force F of the floor reaction force pattern shown in FIG. 5 (a). In the middle stage of rehabilitation, a floor reaction force pattern where the magnitude, the maximum peak, and change rate of the floor reaction force are bigger than those of the initial stage of rehabilitation may be selected so as to provide the floor reaction force F of the floor reaction force pattern shown in FIG. 5(b). In the late stage of rehabilitation, a floor reaction force pattern where the magnitude, the maximum peak, and change rate of the floor reaction force are bigger than those of the middle stage may be selected so as to provide the floor reaction force F of the floor reaction force pattern shown in FIG. 5 (c). In the floor reaction force pattern for the late stage of rehabilitation shown in FIG. 5 (c), the floor reaction force F that is provided is identical to the floor reaction force that a physically unimpaired person receives during walking in a normal manner.

A total amount Fi of the floor reaction force F in each pattern of FIG. 5 (a)-(c) can be represented by the integral value $\int(t1-t0)Fdt$. The floor reaction force total amount Fi corresponds to the total mount of the cranial nerve stimulation. The total amount of the floor reaction force Fi and the slope of the floor reaction force F curve represented by the differential value dF/dt of the floor reaction force F can be regulated according to rehabilitation progress.

Since the torque which controls the floor reaction force can be determined individually for each lower limb joint, different floor reaction force patterns can be separately selected from the patterns shown in FIG. 5 (a)-(c), each for right side or left side lower limb, according to the paralysis degree of each lower limb.

By separately selecting an appropriate floor reaction force pattern for each lower limb using the walking assistance device 1, an asymmetric walking pattern, which is specific to brain paralysis, can be redressed, thereby enabling the patient to walk in a reference symmetric walking pattern.

Figure 7:
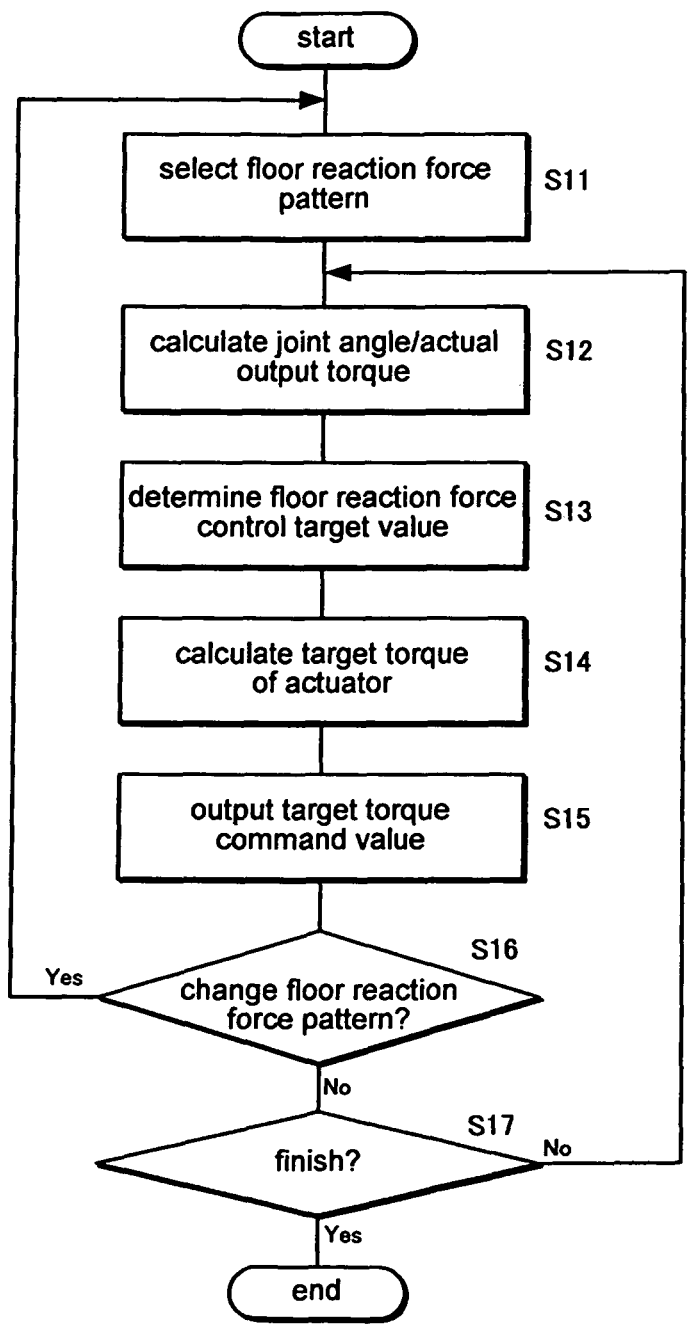
FIG. 7 is a flowchart showing the control flow of the rehabilitation device according to the embodiment 1.

Next, a control flow of the rehabilitation device according to the present invention is explained with reference to the flowchart shown in FIG. 7.

First, a floor reaction force pattern is selected from a plurality of floor reaction force patterns stored in the floor reaction force pattern storing unit 330 through the operating unit 320 (step S11).

Next, the walking status detector 310 calculates each hip joint angle θa and each knee joint angle θb based on the signals from the rotary encoders of the right and left hip joint electric motors 110 and knee joint electric motors 120. The walking status detector 310 also calculates the actual output torque of each of the hip joint electric motors 110 and knee joint electric motors 120 based on the current value of each motor (step S12).

Next, the control target floor reaction force setting unit 340 determines the floor reaction force control target value F* as a dependent value for the hip and knee joint angles (θa and θb) as independent values (step S13).

Next, the target torque calculating unit 350 converts floor reaction force control target value F* into the target torque of the hip joint motors 110 and knee joint motors 120 (step S14).

Next, the control deviation of each motor is calculated from the actual torque value of the motor and the floor reaction force control target value F*, and the target torque command value is sent to the actuator output controller 150 in a feedback compensatory manner (step S15).

Next, the operator selects whether to change the floor reaction force pattern or not through the operating unit 320 (step S16). In case of not changing the floor reaction force pattern, the operator confirms whether to finish or not through the operating unit 320 (step S17). In case of finishing, the control flow ends. On the other hand, in case of choosing not to finish, then the process goes back to step S12 to calculate and upgrade the right and left hip joint angles θa, knee joint angles θb, and actual output torque, repeating steps S13-S17.

In case of changing the floor reaction force pattern, the process goes back to step S11 to change the floor reaction force pattern, repeating steps S12-S17.

To test the effects of the walking assistance device 1 in rehabilitation, a subject person was examined and evaluated for walking motion and brain activity by measuring the glucose metabolism rate using positron emission tomography (PET) and by measuring hemoglobin concentration using near-infrared light under two different conditions: (1) after receiving walking assistance with the walking assistance device 1 being worn on and (2) after walking without the walking assistance device 1.

To conduct this examination, the treadmill 290 was driven at 4 km/h and the subject performed walking exercise thereon for 50 minutes. The subject was administered with 363 MBq Fluorodexyglucose (FDG) 30 minutes after starting the walking exercise, and PET images were obtained 45 minutes after the administration of FDG to determine the standardized uptake value (SUV).

FIG. 8 shows PET images of the lower limbs (lower panel) and hemoglobin concentration of the brain (upper panel). The images shown in FIG. 8 (A) were obtained after performing walking exercise without the walking assistance device 1, while the images shown in FIG. 8 (B) were obtained after performing walking exercise using the walking assistance device 1. Region I is the region where the glucose metabolism rate/brain activity is low. Region II is the region where the glucose metabolism rate/brain activity is higher. Region III indicates the region having the highest glucose metabolism rate/brain activity.

The glucose metabolism rate and brain activity were higher when the walking assistance device 1 was used in the walking exercise as can be seen by comparing (A) and (B) of FIG. 8, indicating the activation of the periarticular muscles of the hip joints and brain by the walking assistance device 1. Such activation of the hip joint periarticular muscles and brain is expected to promote the reconstruction the cerebral tissue.

FIG. 9 shows the increase/decrease rate (mean±2SE) of SUV of each muscle on comparing the values obtained after conducting the walking exercise with the walking assistance device 1 to those obtained after conducting the walking exercise without the walking assistance device 1, based on the above-mentioned PET images obtained from 10 men. SUV is the amount of radioactivity per pixel normalized by administration dose and body weight and can be represented by the following equation.

$$\text{SUV (kg/ml)} = \text{the amount of radioactivity per pixel [Bq/ml]/(dose [Bq]/body weight [kg])}.$$

In FIG. 9, each circle indicates the mean value (for 10 subjects) of the increase/decrease percentage of SUV. For example, if the circle indicates "0", it means that the muscle activity measured after the walking exercise conducted using the walking assistance device 1 was the same as that measured after the walking exercise conducted without using the walking assistance device 1.

FIG. 9 shows that the muscle activity increased in gluteus medius muscle, gluteus minimus, iliac muscle, Vastus lateralis muscle, Vastus medialis muscle, Rectus femoris muscle, Tibialis posterior muscle, Tibialis anterior muscle due to the walking assistance device 1.

Figure 10:
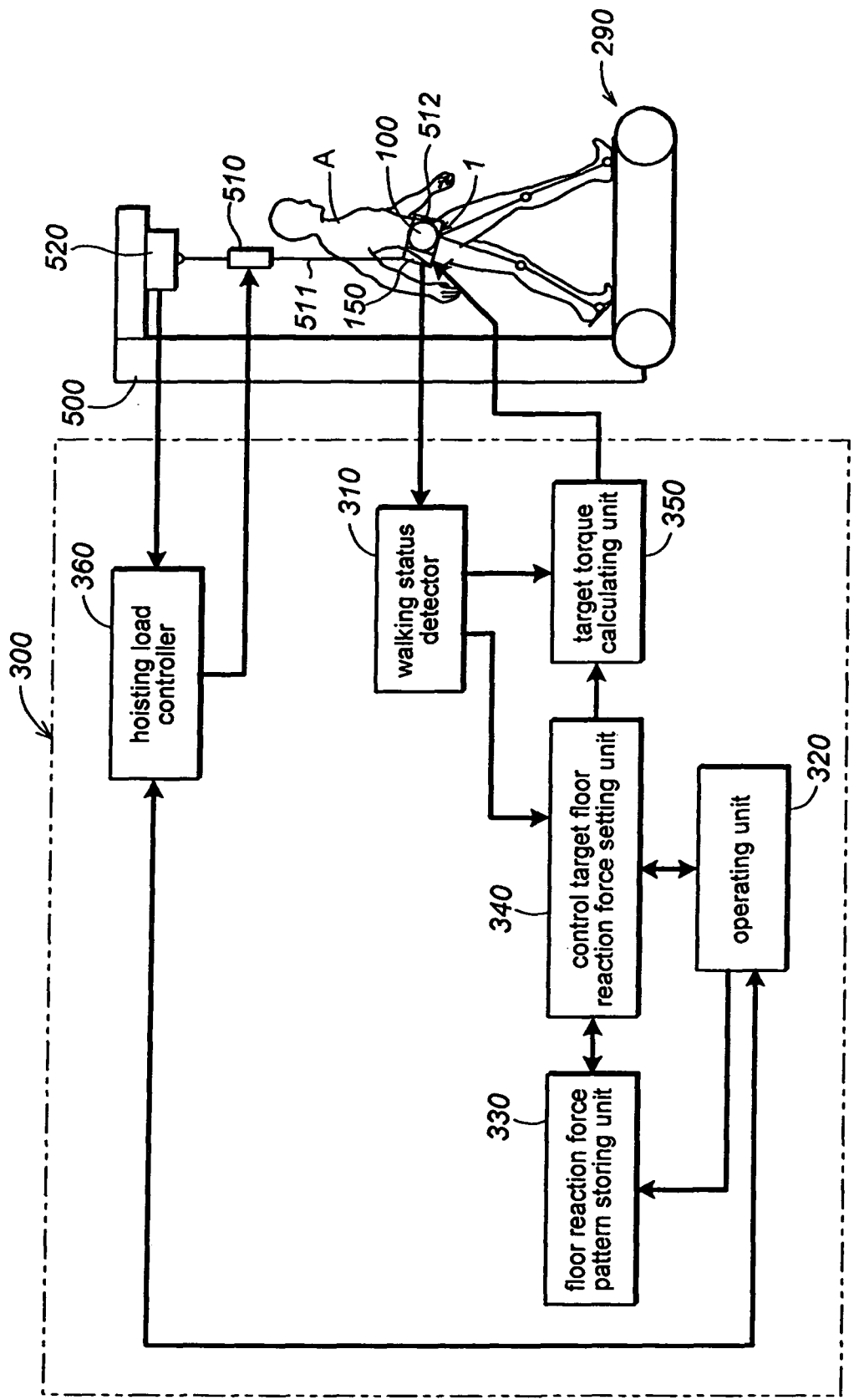
FIG. 10 is a schematic illustration showing another embodiment (embodiment 2) of the rehabilitation device according to the present invention.

FIG. 10 shows another embodiment (embodiment 2) of the rehabilitation device according to the present invention. In FIG. 10, the parts corresponding to those of FIG. 1 are assigned with the same numerals and thus their explanation is omitted.

In this embodiment, the rehabilitation device comprises, a stand 500, a crane 510 mounted to the stand 500, a wire 511 hanged from the crane 510, and a belt 512 connected to the wire 511 and adapted to be worn around the hip and abdomen of a patient A.

In this embodiment, the patient A is partially hoisted at the upper part of the lower limbs in order to reduce the weight load on the lower limbs during walking exercise, thereby enabling rehabilitation for patients incapable of standing and walking on their own. The hoisting load of crane 510 is controlled by a hoisting load controller 360 to increase or decrease the floor reaction force that the patient receives.

The hoisting load controller 360 may detect the hoisting load of the crane 510 through a load cell 520 mounted to a portion of the stand 500 where the crane 510 is attached, and control the hoisting load of the crane 510 in a feedback compensatory manner. The hoisting load controlled by the hoisting load controller 360 can be set through the operating unit 320.

Figure 11:
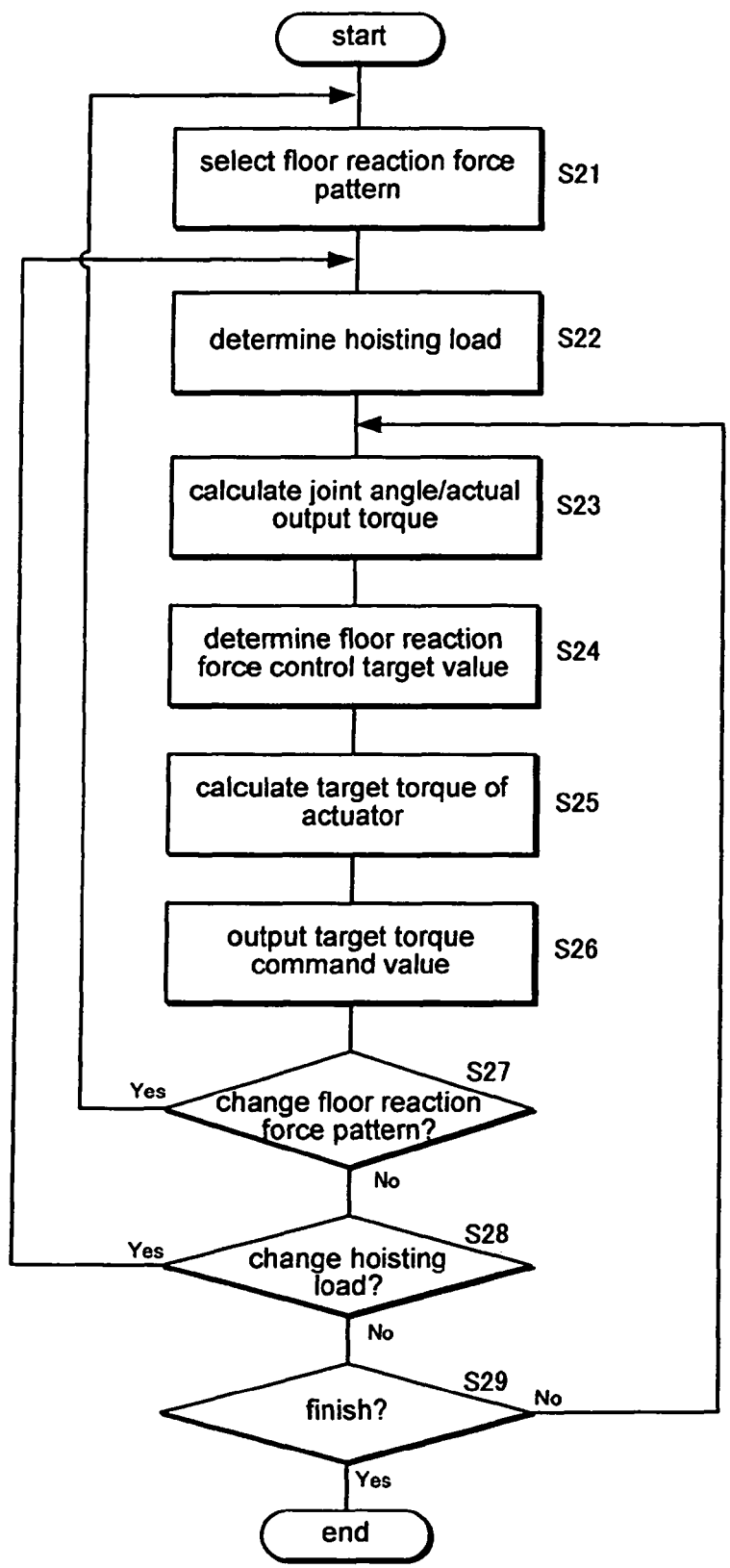
FIG. 11 is a flowchart showing the control flow of the rehabilitation device according to the embodiment 2.

Next, the control flow of the rehabilitation device according to this embodiment is explained with reference to the flowchart shown in FIG. 11.

First, a floor reaction force pattern is selected from a plurality of floor reaction force patterns stored in the floor reaction force pattern storing unit 330 through the operating unit 320 (step S21). Next, a hoisting load of the crane 510 is set through the operating unit 320 (step S22).

Next, the walking status detector 310 calculates each hip joint angle θa and each knee joint angle θb based on the signals from the rotary encoders of the right and left hip joint electric motors 110 and knee joint electric motors 120. The walking status detector 310 also calculates the actual output torque of each of the hip joint electric motors 110 and knee joint electric motors 120 based on the current value of each motor (step S23).

Next, the control target floor reaction force setting unit 340 determines the floor reaction force control target value F* as a dependent value for the hip and knee joint angles (θa and θb) as independent values (step S24).

Next, the target torque calculating unit 350 converts the floor reaction force control target value F* into the target torque of the hip joint electric motors 110 and knee joint electric motors 120 (step S25).

Next, the control deviation of each motor is calculated from the actual torque value of the motor and the floor reaction force control target value F*, and the target torque command value is sent to the actuator output controller 150 in a feedback compensatory manner (step S26).

Next, the operator selects whether to change the floor reaction force pattern or not through the operating unit 320 (step S27). In case of not changing the floor reaction force pattern, the operator selects whether to change the hoisting load using the operating unit 320 (step S28). In case of not changing the hoisting load, the operator confirms whether to finish or not through the operating unit 320 (step S29). In case of finishing, the control flow ends. On the other hand, in case of choosing not to finish, then the process goes back to step S23 to calculate and upgrade the right and left hip joint angles θa, knee joint angles θb, actual output torque, repeating steps S24-S29.

In case of changing the floor reaction pattern, the process goes back to step S21 to change the floor reaction force pattern to another pattern that is to be used, repeating steps S22-S29. In case of changing the hoisting load, the process goes back to step S22 to change the hoisting load of the crane 510, repeating steps S23-S29.

Figure 12:
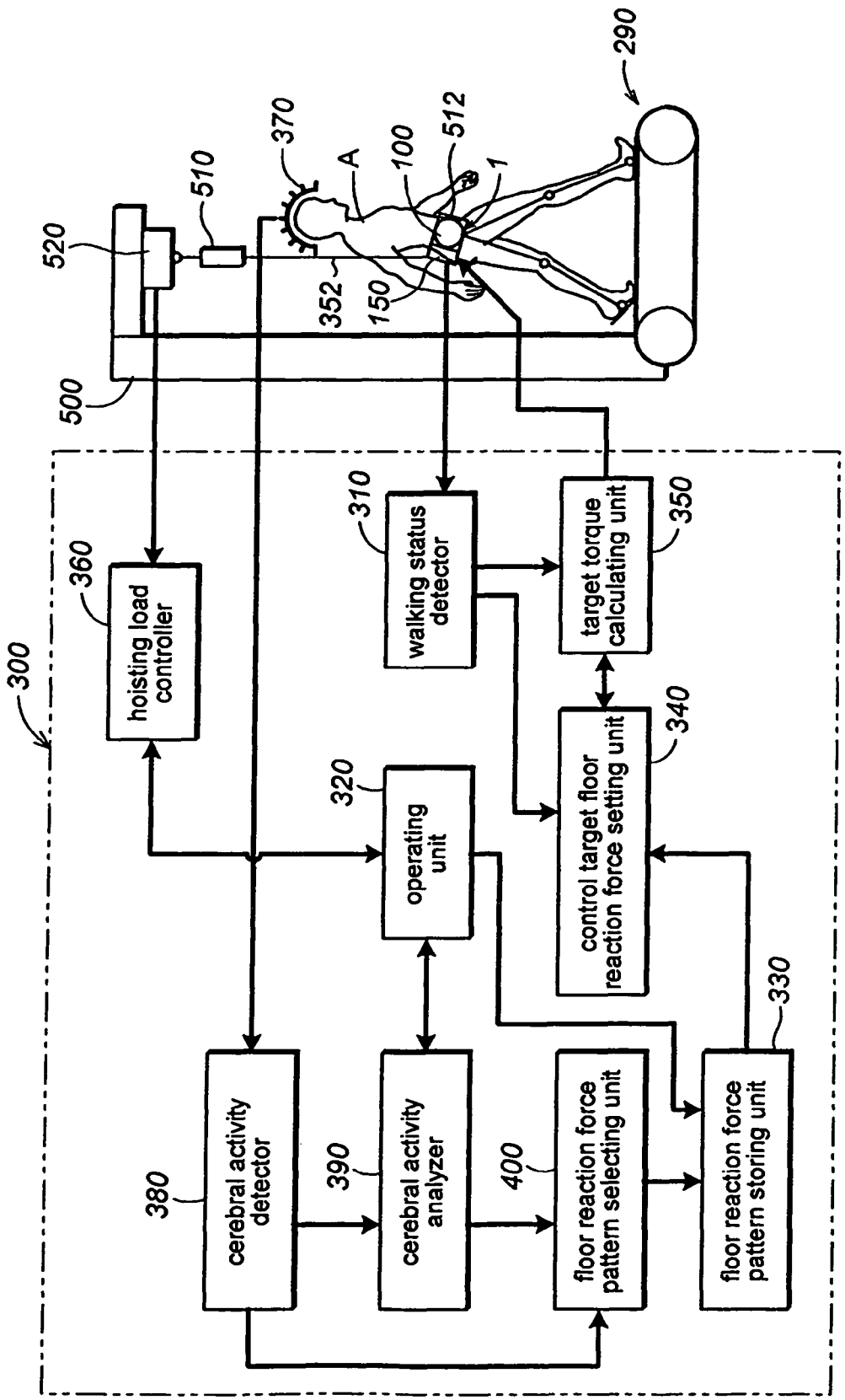
FIG. 12 is a schematic illustration showing yet another embodiment (embodiment 3) of the rehabilitation device according to the present invention.

FIG. 12 shows yet another embodiment (embodiment 3) according to the rehabilitation device of the present invention. In FIG. 12, the parts corresponding to those of FIG. 1 and FIG. 10 are assigned with the same numerals, and thus their explanation is omitted.

In this embodiment, a patient A wears on his/her head a cerebral activity measuring device 370 for measuring the brain activity over time. The cerebral activity measuring device 370 may be a head gear type and comprises, for example, electroencephalograph, magnetoencephalograph, near-infrared spectrometer to obtain electroencephalogram and values indicating brain activity such as brain magnetic field and oxygen metabolism. The signals of the values indicating brain activity obtained from cerebral activity measuring device 370 then are inputted into a cerebral activity detector 380.

The cerebral activity detector 380 quantitatively-detects the cerebral activity of the patient A during walking based on the value signals received from the cerebral activity measuring device 370. The cerebral activity detector 380 can detect separately the activity of the right motor area and that of the left motor area.

The cerebral activity detector 380 is connected to a cerebral activity analyzer 390. The cerebral activity analyzer 390 analyzes the information regarding the activity of the right motor area and left motor area received from the cerebral activity detector 380 to reveal the stimuli distribution of the right motor area and left motor area.

Then, the analysis result obtained from the cerebral activity analyzer 390 is sent to the operating unit 320 and a floor reaction force pattern selecting unit 400.

The monitor of the operating unit 320 shows the analysis result regarding the cerebral activity obtained from the cerebral activity analyzer 390. Therefore, the operator (e.g., physical therapist) can select a floor reaction force pattern from the floor reaction force pattern storing unit 330 in manual mode while watching the monitor.

The floor reaction force pattern selecting unit 400 can automatically select the optimum floor reaction force pattern based on the cerebral activity detected by the cerebral activity detector 380 and brain analysis result obtained from the cerebral activity analyzer 390.

The floor reaction force pattern selecting unit 400 can operate in an average mode in which it averages values of the brain activity of the right and left motor areas, and then selects a floor reaction force pattern based on this brain activity average value, or in a right-and-left individual mode in which it separately selects two floor reaction force patterns each for right or left lower limb based on the activity of the right motor area and that of the left motor area. The mode can be set or changed through the operating unit 320.

In this embodiment, the floor reaction force pattern can be selected manually or automatically while checking the activity of the right and left motor areas of the brain and brain reconstruction by monitoring the cerebral activity in real-time, thereby enabling to plan and perform appropriate and effective rehabilitation.

Figure 13:
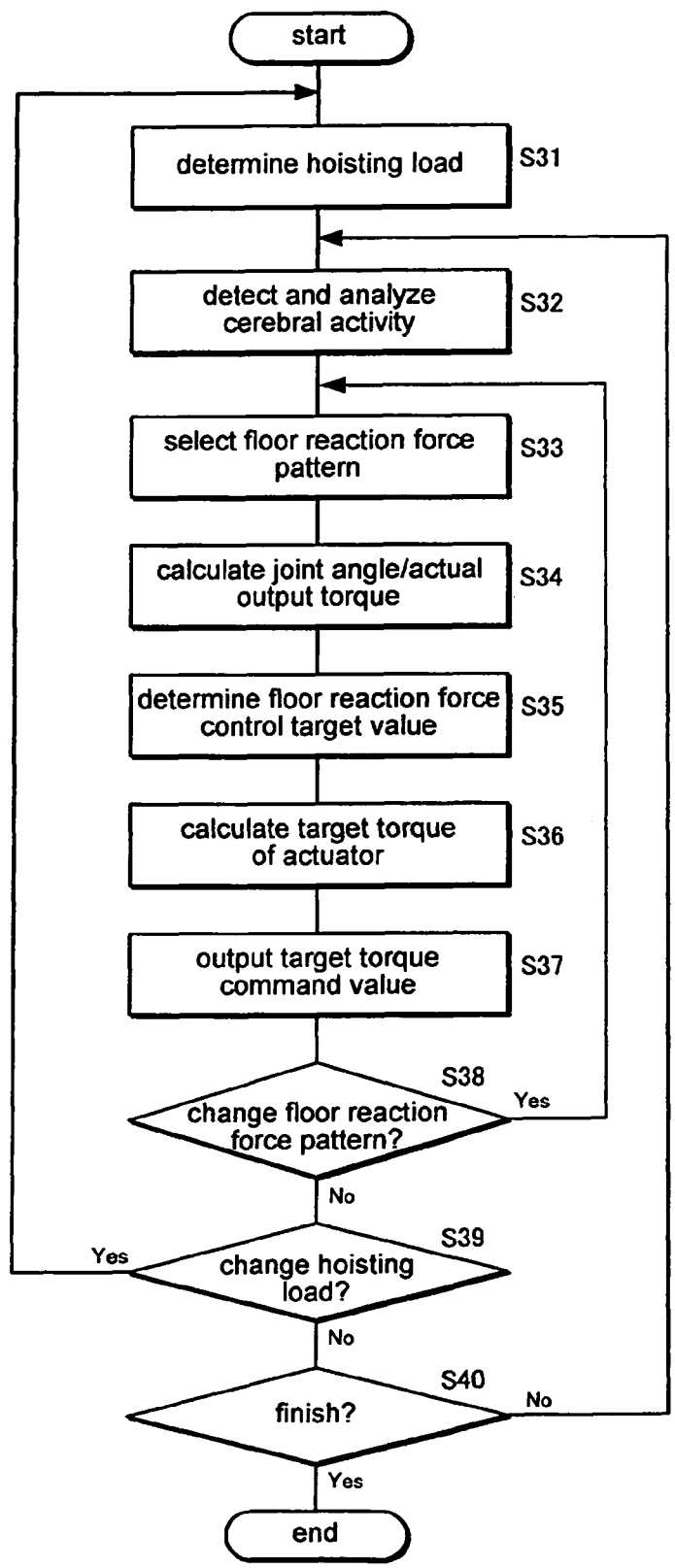
FIG. 13 is a flowchart showing the control flow of the rehabilitation device according to the embodiment 3.

Next, the control flow of the rehabilitation device according to this embodiment is explained with reference to the flowchart shown in FIG. 13.

First, a hoisting load of the crane 510 is set through the operating unit 320 (step S31).

Next, the cerebral activity detector 380 detects the cerebral activity, and the cerebral activity analyzer 390 analyses the cerebral activity (step S32).

Next, a floor reaction force pattern is selected from the plurality of floor reaction force patterns stored in the floor reaction force pattern storing unit 330 based on the detected and analyzed data regarding the cerebral activity (step S33). A floor reaction force pattern defaulted as an initial floor reaction force pattern may be selected for the initial stage of the rehabilitation.

Next, the walking status detector 310 calculates each hip joint angle θa and each knee joint angle θb based on the signals from the rotary encoders of the right and left hip joint electric motors 110 and knee joint electric motors 120. The walking status detector 310 also calculates the actual output torque of each of the hip joint electric motors 110 and knee joint electric motors 120 based on the current value of each motor (step S34).

Next, the control target floor reaction force setting unit 340 determines the floor reaction force control target value F* as a dependent value for the hip and knee joint angles (θa and θb) as independent values (step S35).

Next, the target torque calculating unit 350 converts the floor reaction force control target value F* into target torque of the hip joint electric motors 110 and knee joint electric motors 120 (step S36).

Next, the control deviation of each motor is calculated from the actual torque value of the motor and the floor reaction force control target value F*, and the target torque command value is sent to the actuator output controller 150 in a feedback compensatory manner (step S37).

Next, the operator selects whether to change the floor reaction force pattern or not through the operating unit 320 (step S38). In case of not changing the floor reaction force pattern, the operator selects whether to change the hoisting load using the operating unit (step S39). In case of not changing the hoisting load, the operator confirms whether to finish or not through the operating unit 320 (step S40). In case of finishing, the control flow ends. On the other hand, in case of choosing not to finish, then the process goes back to step S32 to detect and analyze the current cerebral activity and upgrade these data, repeating steps S33-40.

In case of changing the floor reaction pattern, the process goes back to step S33 to change the floor reaction force pattern to another pattern that is to be used, repeating steps S34-S40. In case of changing the hoisting load, the process goes back to step S31 to change the hoisting load of the crane 510 repeating steps S32-S40.

In addition to rehabilitation for patients suffering from motor impairment of limbs caused by cerebral infraction or cerebral stroke, the rehabilitation device according to the present invention can also be used for rehabilitation for elders aiming at enhancing their recovery in motor function and recognition ability.

The invention claimed is:

1. A rehabilitation device including a walking assistance device having an actuator which is operable to generate and provide torque to at least one lower limb joint of a wearer wearing the walking assistance device, said rehabilitation device comprising:
    a floor reaction force pattern storing unit configured to store a plurality of different reference floor reaction force patterns, the plurality of different reference floor reaction force patterns being stored in the floor reaction force pattern storing unit prior to use of the rehabilitation device by the wearer;
    a floor reaction force pattern selecting unit for selecting a reference floor reaction force pattern from the plurality of reference floor reaction force patterns;
    a control target floor reaction force setting unit for determining a control target floor reaction force based on the reference floor reaction force pattern selected by the floor reaction force pattern selecting unit;
    a target torque calculating unit for calculating a target torque of the actuator to achieve the control target floor reaction force determined by the control target floor reaction force setting unit; and
    an actuator output controller for controlling output of the actuator such that the actuator generates a torque matching the target torque calculated by the target torque calculating unit;
    wherein an applied floor reaction force that the wearer receives is variable by an application of torque generated by the actuator.

2. The rehabilitation device according to claim 1, wherein each of the plurality of reference floor reaction force patterns is based on a standard floor reaction force which a physically unimpaired person receives during walking in a normal manner.

3. The rehabilitation device according to claim 1, wherein each of the reference floor reaction force patterns stored in the floor reaction force pattern storing unit is a pattern in which a floor reaction force varies according to change in a joint angle of the lower limb joint.

4. The rehabilitation device according to claim 1, wherein the floor reaction force pattern selecting unit selects a reference floor reaction force pattern from the plurality of reference floor reaction force patterns through external manipulation.

5. The rehabilitation device according to claim 1, further comprising:
    a caterpillar-type treadmill on which the wearer walks;
    a hoisting unit for partially-hoisting an upper part of lower limbs of the wearer on the treadmill; and
    a hoisting load controller for controlling a hoisting load of the hoisting unit.

6. The rehabilitation device according to claim 1, further comprising a walking status detector that provides an actual floor reaction force to the target torque calculating unit.

7. The rehabilitation device according to claim 1, wherein the control target floor reaction force setting unit receives the reference floor reaction force pattern from the floor reaction force pattern selecting unit to determine the control target floor reaction force as a mathematical function of a joint angle, and provides the determined control target floor reaction force to the target torque calculating unit.

8. The rehabilitation device according to claim 1, wherein the target torque calculating unit is configured to convert the control target floor reaction force into the target torque based on a correlation property between the control target floor reaction force and the target torque.

9. The rehabilitation device according to claim 1,
    wherein the actuator comprises:
        a first motor for providing torque to a first lower limb joint of the wearer; and
        a second motor for providing torque to a second lower limb joint of the wearer.

10. The rehabilitation device according to claim 9, wherein the first lower limb joint is a hip joint and the second lower limb joint is a knee joint.

11. The rehabilitation device according to claim 9, further comprising a walking status detector, wherein:
    the first motor comprises a first encoder;
    the second motor comprises a second encoder; and
    said walking status detector:
        receives a first current value from the first motor;
        receives a second current value from the second motor;
        calculates a flexion angle of the first lower limb joint, $\theta a$, based on a signal from the first encoder;
        calculates a flexion angle of the second lower limb joint, $\theta b$, based on a signal from the second encoder; and
        provides an actual output torque of each motor to the target torque calculating unit based on the first current value and the second current value of each respective motor.

12. A rehabilitation device comprising:
    a walking assistance device having an actuator which is operable to generate torque and to provide said torque to a lower limb joint of a wearer wearing the walking assistance device;
    a floor reaction force pattern storing unit configured to store a reference floor reaction force pattern;
    a control target floor reaction force setting unit for determining a control target floor reaction force based on the reference floor reaction force pattern stored in the floor reaction force pattern storing unit;
    a target torque calculating unit for calculating a target torque of the actuator to achieve the control target floor reaction force determined by the control target floor reaction force setting unit;
    an actuator output controller for controlling output of the actuator such that the actuator generates a torque matching the target torque calculated by the target torque calculating unit; and
    a cerebral activity detector for quantitatively-detecting brain activity of the wearer during walking;
    wherein the floor reaction force pattern storing unit is configured to store a plurality of reference floor reaction force patterns, each different from each other;

wherein the rehabilitation device further comprises a floor reaction force pattern selecting unit for selecting a reference floor reaction force pattern from the plurality of reference floor reaction force patterns according to the brain activity quantitatively-detected by the cerebral activity detector;

wherein an applied floor reaction force that the wearer receives is variable by the application of torque generated by the actuator;

and wherein the control target floor reaction force setting unit is configured to determine the control target floor reaction force based on the reference, floor reaction force pattern selected by the floor reaction force pattern selecting unit.

13. The rehabilitation device according to claim 12, wherein the cerebral activity detector is configured to detect brain activity of a right motor area and of a left motor area of the brain, and the floor reaction force pattern selecting unit is configured to average values of the brain activity of the right motor area and the left motor area to obtain a brain activity average value based on which the floor reaction force pattern selecting unit is configured to select the reference floor reaction force pattern.

14. The rehabilitation device according to claim 12, wherein the cerebral activity detector is configured to detect brain activity of a right motor area and of a left motor area of the brain, and the floor reaction force pattern selecting unit is configured to separately select a reference floor reaction force patterns for each of a right side lower limb and a left side lower limb, based on the detected brain activity of the right motor area and the left motor area, respectively.

15. A method for controlling a rehabilitation device using a walking assistance device having an actuator which provides torque to a lower limb joint of a wearer wearing the walking assistance device, comprising:

storing a plurality of different reference floor reaction force patterns prior to use of the rehabilitation device by the wearer;

selecting a reference floor reaction force pattern from the plurality of different reference floor reaction force patterns;

determining a control target floor reaction force according to the reference floor reaction force pattern;

using a target torque calculating unit to calculate a target torque of the actuator for achieving the control target floor reaction force; and controlling output of the actuator such that the actuator generates a torque matching the target torque calculated by the target torque calculating unit;

wherein an applied floor reaction force that the wearer receives is increased and decreased by an application of the torque generated by the actuator.

16. The method for controlling the rehabilitation device according to claim 15, wherein the reference floor reaction force pattern is varied depending on a progress of the wearer in a rehabilitation process of the wearer.

* * * * *